United States Patent [19]

Kompis et al.

[11] 4,203,980

[45] May 20, 1980

[54] BENZYLPYRIMIDINE DERIVATIVES

[75] Inventors: Ivan Kompis, Oberwil; Alexander E. Wick, Riehen, both of Switzerland

[73] Assignee: Hoffmann-La Roche Inc., Nutley, N.J.

[21] Appl. No.: 900,357

[22] Filed: Apr. 26, 1978

[30] Foreign Application Priority Data

May 5, 1977 [LU] Luxembourg .......................... 77269
Mar. 10, 1978 [CH] Switzerland ........................ 2650/78

[51] Int. Cl.² .................. A61K 31/635; C07D 239/48
[52] U.S. Cl. ..................................... 424/229; 424/228; 424/251; 544/325; 568/442; 568/433; 568/649; 260/465 E; 260/465 F; 260/465 D; 260/338; 260/340.7; 260/340.9 R
[58] Field of Search ................. 544/325; 424/229, 251

[56] References Cited

U.S. PATENT DOCUMENTS

| | | | |
|---|---|---|---|
| 3,985,876 | 10/1976 | Hazlett et al. | 424/229 |
| 3,996,356 | 12/1976 | Grunberg | 424/229 |
| 4,033,962 | 7/1977 | Rosen | 544/325 |

FOREIGN PATENT DOCUMENTS 1388213   3/1975   United Kingdom ..................... 544/325

*Primary Examiner*—Paul M. Coughlan, Jr.
*Attorney, Agent, or Firm*—Jon S. Saxe; George M. Gould; Peter R. Shearer

[57] ABSTRACT

Benzylpyrimidines of the formula

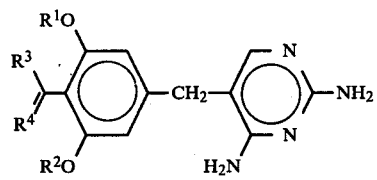

wherein $R^1$ and $R^2$, independently, are $C_{1-6}$-alkyl, $R^3$ is $C_{1-3}$-alkyl and $R^4$ is methylene or $C_{2-4}$-alkylidene and physiologically compatible acid addition salts thereof, are described. The compounds of formula I are useful as antibacterial agents and as potentiators of sulfonamides.

16 Claims, No Drawings

BENZYLPYRIMIDINE DERIVATIVES

BRIEF SUMMARY OF THE INVENTION

The invention relates to compounds characterized by the formula

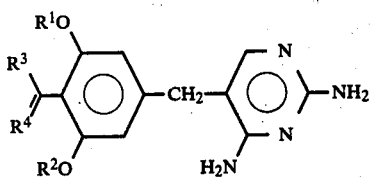

I wherein $R^1$ and $R^2$, independently, are $C_{1-6}$-alkyl, $R^3$ is $C_{1-3}$-alkyl and $R^4$ is methylene or $C_{2-4}$-alkylidene and physiologically compatible or acceptable acid addition salts thereof.

In another aspect, the invention relates to pharmaceutical compositions which contain compounds of formula I.

DETAILED DESCRIPTION OF THE INVENTION

The benzylpyrimidines of the invention are compounds of the formula

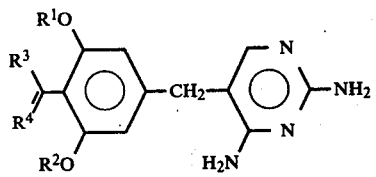

I wherein $R^1$ and $R^2$, independently, are $C_{1-6}$-alkyl, $R^3$ is $C_{1-3}$-alkyl and $R^4$ is methylene or $C_{2-4}$-alkylidene or a physiologically acceptable acid addition salt thereof.

As used herein, the $C_{1-6}$-alkyl groups are straight-chain and branched-chain alkyl groups, such as, methyl, ethyl, propyl, isopropyl, butyl, isobutyl, sec.butyl, tert.butyl or the like. The $C_{2-4}$-alkylidene groups comprise ethylidene, propylidene, isopropylidene, butylidene, isobutylidene and sec.butylidene.

The preferred benzylpyrimidines of formula I of the invention are, on the one hand, those wherein $R^1$ and $R^2$, independently, are $C_{1-3}$-alkyl, especially methyl or ethyl, and, on the other hand, those wherein $R^3$ is $C_{1-3}$-alkyl and $R^4$ is methylene or ethylidene.

Exemplary of the compounds of formula I of the invention are:
- 2,4-diamino-5-(4-isopropenyl-3,5-dimethoxybenzyl)-pyrimidine;
- 2,4-diamino-5-(3-ethoxy-4-isopropenyl-5-methoxybenzyl)-pyrimidine;
- 2,4-diamino-5-(3,5-diethoxy-4-isopropenylbenzyl)-pyrimidine;
- 2,4-diamino-5-{3,5-dimethoxy-4-[2-(2-butenyl)]-benzyl}-pyrimidine;
- 2,4-diamino-5-{3,5-diethoxy-4-[2-(2-butenyl)]-benzyl}-pyrimidine;
- 2,4-diamino-5-{3,5-dimethoxy-4-[3-(2-pentenyl)]-benzyl}-pyrimidine; and
- 2,4-diamino-5-{3,5-diethoxy-4-[3-(2-pentenyl)]-benzyl}-pyrimidine.

In accordance with the present invention, the benzylpyrimidines, that is, the compounds of formula I and their salts, are prepared by
(a) dehydrating a compound of the formula

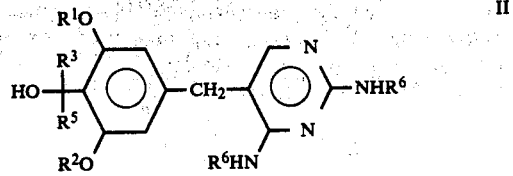

II wherein $R^1$, $R^2$ and $R^3$ are as previously described, $R^5$ is $C_{1-4}$-alkyl and $R^6$ is hydrogen or an amino protecting group
and, if desired, simultaneously cleaving the amino protecting group that may be present, or
(b) reacting a compound of the formula

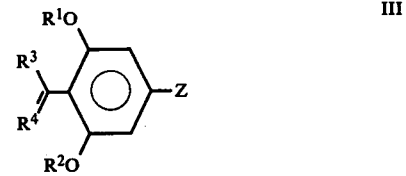

III wherein $R^1$, $R^2$, $R^3$ and $R^4$ are as previously described and Z is a group of the —$CH_2$—CH(C-N)—CH(OR^7)_2$ or —$CH_2$—$C(=CHY)CN$, wherein $R^7$ is $C_{1-4}$-alkyl or both $R^7$s taken together are $C_{1-4}$-alkylene and Y is a leaving group
with guanidine or a guanidine salt, or,
(c) etherifying the hydroxy group in a compound of the formula

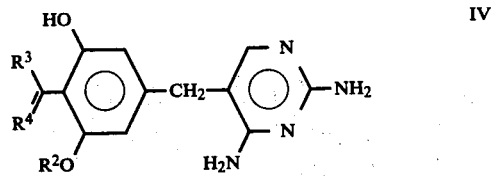

IV wherein $R^2$, $R^3$ and $R^4$ are as previously described to $C_{1-6}$-alkoxy, or
(d) reductively removing the substituent X from a compound of the formula

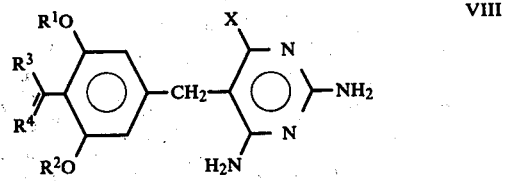

VIII wherein $R^1$, $R^2$, $R^3$ and $R^4$ as the previously described and X is chlorine or bromine
and, if desired, converting a compound of formula I so obtained into an acid addition salt.

According to process embodiment (a) of the present invention, a compound of formula II is dehydrated. The dehydration can be carried out in a known manner, that is, according to methods which are known for cleavage of water, from secondary and tertiary alcohols as described, for example, in Fieser & Fieser, Reagents for Organic Synthesis, Volumes 1–5, John Wiley & Sons, Inc., N.Y., 1967–1975. The dehydration is preferably carried out in the presence of an acid dehydrating agent, for example, an inorganic or organic acid, such as, hydrochloric acid, hydrobromic acid or p-toluenesulfonic acid, conveniently in aqueous-alcoholic solution at a pH below 5 and a temperature in the range of room temperature to the reflux temperature of the mixture. The dehydration can, however, also be carried out in a suspension using an organic solvent such as tetrahydrofuran, dioxane, dimethylsulfoxide or the like. The dehydration can also be carried out in a purely thermal manner, that is, by heating in a suitable solvent to a temperature in the range of from about 100° C. to the reflux temperature of the mixture.

Amino protecting groups, for example, acyl groups, such as, formyl, acetyl and trifluoroacetyl; alkoxycarbonyl groups, such as, tert.butoxycarbonyl; or aralkoxycarbonyl groups, such as, benzyloxycarbonyl, which may be present in a compound of formula II, are cleaved under the conditions of an acid dehydration with the formation of amino groups.

According to process embodiment (b) of the present invention, a compound of formula III is reacted with guanidine or a guanidine salt. The reaction can be carried out in a known manner, for instance, in an organic solvent, such as, an alkanol, for example, methanol or ethanol; dimethylformamide; dimethylsulfoxide; or N-methylpyrazolone at a temperature in the range of from about 25° C. to 200° C., preferably in the range of from about 50° C. to 170° C. Examples of guanidine salts which can be used are the carbonate and the hydrochloride. Exemplary of the leaving groups denoted by Y in compounds of formula III are alkoxy, such as methoxy, ethoxy, propoxy or the like; alkylthio; amino; amino groups substituted by aliphatic aromatic or heterocyclic groups, such as, alkylamino, benzylamino, arylamino, for instance, optionally substituted anilino or naphthylamino, dialkylamino, pyrrolidino, piperidino, piperazino or morpholino. Especially preferred are anilino, the phenyl ring of which can optionally carry one or more halogen, alkyl or alkoxy substituents.

The starting materials of formula III can be prepared according to the following Formula Scheme wherein $R^1$, $R^2$, $R^3$, $R^4$, $R^5$, $R^7$ and Y are as previously described.

Formula Scheme

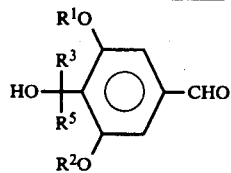

(VI)

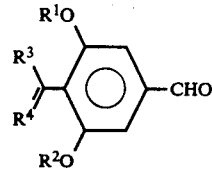

(V)

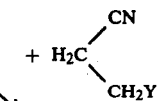

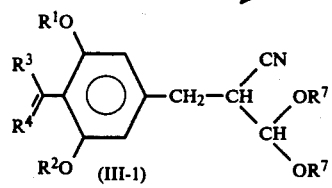

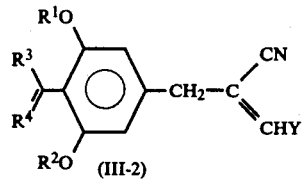

(III-1)    (III-2)

With reference to the foregoing Formula Scheme, a compound of formula VI, disclosed, for example, in Belgian Pat. No. 818,131, is dehydrated in a manner analogous to that described hereinbefore in connection with process embodiment (a) to give a compound of formula V which, according to the methods described in Belgian Pat. No. 818,131, is then converted either by condensation with a β-alkoxypropionitrile and subsequent addition of an alkanol of the formula $R^7OH$ into a compound of formula III-1 or by base-catalyzed condensation with a β-substituted-propionitrile of the formula Y—CH₂—CH₂—CN in a polar aprotic solvent into a compound of formula III-2.

The compounds of formula V are novel and also form part of the present invention.

By reacting a compound of formula V, a substituted benzaldehyde, with malonic acid dinitrile there is obtained a compound of the formula

VII

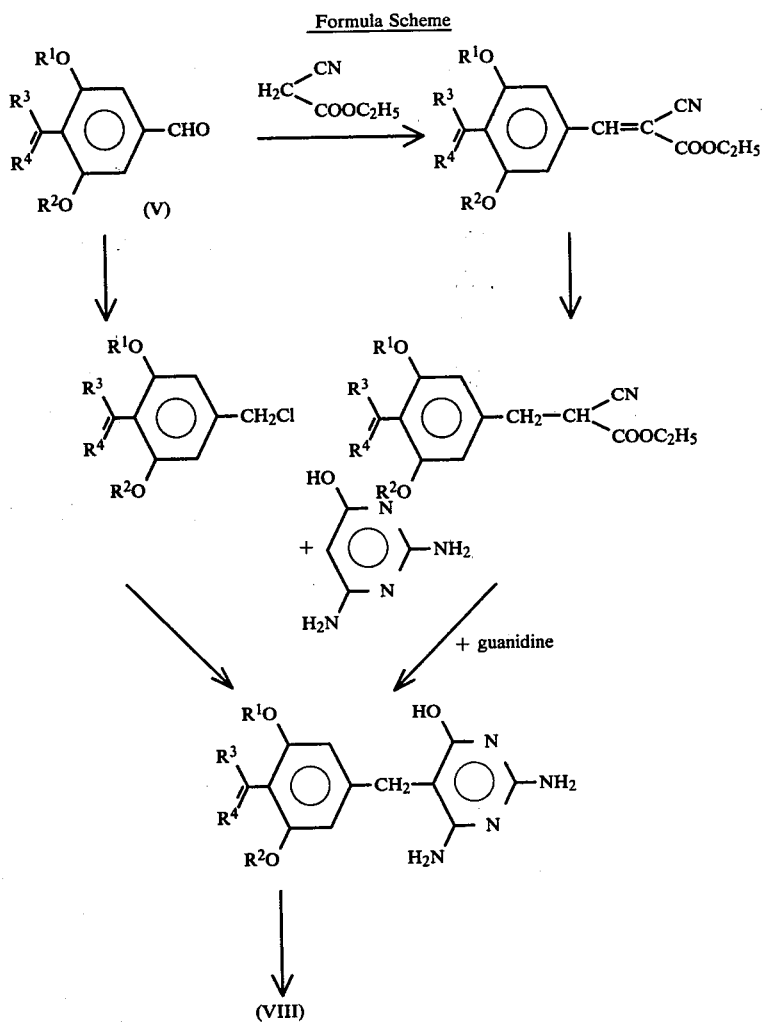

wherein $R^1$, $R^2$, $R^3$ and $R^4$ are as previously described, which can readily be converted into a compound of formula III-2, wherein Y is amino, by reduction with a complex metal hydride, for example, sodium borohydride, at room temperature.

with excess sodium ethylmercaptide in dimethylformamide.

The removal of the chlorine or bromine atom denoted by X in a compound of formula VIII in accordance with process embodiment (d) of the present invention can be carried out by treatment with a reducing agent in a known manner. A suitable reducing agent is, for example, zinc, preferably in amalgamated form, in acetic acid solution.

The starting materials of formula VIII can be prepared in a known manner, for example, as illustrated in the following Formula Scheme wherein $R^1$, $R^2$, $R^3$ and $R^4$ are as previously described.

Formula Scheme (VIII)

According to process embodiment (c) of the present invention, the hydroxy group in a compound of formula IV is etherified. The etherification is carried out in a known manner by reaction with an alkylating agent of the formula $R^1X$ wherein $R^1$ is as previously described and X is, for example, chlorine, bromine or iodine. This embodiment of the process is especially suitable for the preparation of compounds of formula I wherein $R^1$ and $R^2$ are independently different $C_{1-6}$-alkyl groups.

The starting materials of formula IV can be prepared in a known manner. They can be prepared, for example, very readily and in high yield by the partial demethylation of a 3,5-dimethoxybenzyl compound of formula I To prepare acid addition salts, especially of salts which can be used in pharmaceutical preparations, that is, physiologically or pharmaceutically compatible or acceptable salts, there come into consideration inorganic and organic acids which are customarily used for this purpose for example, hydrochloric acid, sulfuric acid, phosphoric acid, formic acid, acetic acid, oxalic acid, tartaric acid, maleic acid, benzoic acid, succinic acid, fumaric acid, levulinic acid, salicylic acid, citric acid, isocitric acid, adipic acid, lactic acid, α-ketoglutaric acid, malic acid, malonic acid, glyceric acid, mevalonic acid, glucuronic acid, neuraminic acid, glutaric acid, aspartic acid, gluconic acid, mandelic acid, ascorbic acid, lactobionic acid, glucoheptonic acid, glutamic acid, nicotinic acid, pantothenic acid, folic acid, adenylic acid, geranylic acid, cytidylic acid and inosic acid.

The compounds of formula I have antibacterial activity. More specifically, the compounds of formula I inhibit the bacterial dihydrofolic acid reductase (DHFR) and, moreover, potentiate the activity of sulfonamides and other dihydrofolic acid synthetase inhibitors. Exemplary of the sulfonamides which are potentiated by the compounds provided by the present invention are sulfadiazine, sulfadimethoxine, sulfadoxine, sulfamethoxazole, sulfisoxazole, sulfamoxole, 3-sulfanilamido-4,5-dimethylisoxazole, sulfalene, sulfamerazine, sulfameter, sulfamethazine and 6-methoxy-4-sulfanilamido-pyrimidine. The compounds of formula I are qualitatively comparable with structurally analogous benzylpyrimidines, for example, 2,4-diamino-5-(3,4,5-trimethoxybenzyl)-pyrimidine or 2,4-diamino-5-(3,5-dimethoxy-4-methylbenzyl)-pyrimidine which are noteworthy for their activity. Quantitatively, however, compared with known compounds, the compounds of formula I of the present invention are characterized by lower 50% inhibitory concentrations of the bacterial DHFR, for example, in the case of E. coli, and by substantially higher Q-values, that is 50% inhibition of the DHFR in the case of rats/50% inhibition of the DHFR in the case of E. coli, which represents a measurement of the selectivity of the inhibition of the bacterial DHFR.

The Q-values for three representative compounds of formula I of the present invention are set forth in the Table which follows:

$$\text{(IX)}$$

Structure: 2,4-diaminopyrimidine with $NH_2$ groups, N atoms, $H_2N$, linked via $CH_2$ to a benzene ring bearing $R^1$, $R^2$, $R^3$.

| Compound | $R^1$ | $R^2$ | $R^3$ | 50% inhibition of the DHFR (mol/l) × $10^{-8}$ | |
|---|---|---|---|---|---|
| | | | | E. coli | Rat/E. coli |
| 1 | $OC_2H_5$ | $-C(CH_3)=CH_2$ | $OC_2H_5$ | 0.22 | 160 000 |
| 2 | $OCH_3$ | $-C(CH_3)=CH_2$ | $OCH_3$ | 0.34 | 440 000 |
| 3 | $OCH_3$ | $-C(CH_3)=CH_2$ | $OC_2H_5$ | 0.32 | >100 000 |

The benzylpyrimidines of formula I provided by the present invention can be used in the form of pharmaceutical preparations, having direct or delayed liberation of the active ingredient, in association with a compatible pharmaceutical carrier material. Such carrier material can be an organic or inorganic inert carrier material suitable for oral, rectal or parenteral administration, for example, water, gelatin, gum arabic, lactose, starch, magnesium stearate, talc, vegetable oils, polyalkyleneglycols, petroleum jelly, etc. The pharmaceutical preparations can be made up in a solid form, for example, as tablets, dragees, suppositories or capsules, in a semisolid form, for example, as salves or in a liquid form, for example, as solutions, suspensions or emulsions. The pharmaceutical preparations may be sterilized and/or may contain additional adjuvants, such as preserving, stabilizing, wetting or emulsifying agents, flavor-improving agents, salts for varying the osmotic pressure or buffer substances. The pharmaceutical preparations can be provided in a known manner.

In pharmaceutical preparations containing a benzylpyrimidine of formula I of this invention and a sulfonamide, the weight ratio of the two components to one another can vary within wide limits. The weight ratio can be in the range of from 1:40 to 10:1, preferably amounts to 1:5 to 5:1. A tablet can contain, for example, 80 to 400 mg. of a compound of formula I and 400–80 mg. of a sulfonamide. In the case of preparations containing a compound of formula I as the sole active ingredient, 100–1000 mg. can be considered as the guideline for a single dose which, depending on requirements, can be administered once daily or several times daily.

The Examples which follow further illustrate the present invention:

EXAMPLE 1

Preparation of 2,4-diamino-5-(4-isopropenyl-3,5-dimethoxybenzyl)-pyrimidine

A suspension of 31.8 g. of 4-[(2,4-diamino-5-pyrimidyl)methyl]-2,6-dimethoxy-α,α-dimethylbenzyl alcohol in 600 ml. of methanol and 60 ml. of concentrated hydrochloric acid was heated to reflux while stirring for 1 hour and subsequently evaporated to dryness under reduced pressure. The residue was suspended in 300 ml. of water. The suspension, after the addition of 25% aqueous ammonia solution up to a pH of about 10 while cooling with ice, was stirred for an additional hour. The solid residue was removed by filtration under suction, washed neutral with water and dried to yield 27.6 g. (92%) of 2,4-diamino-5-(4-isopropenyl-3,5-dimethoxybenzyl)-pyrimidine having a melting point of 228°–229° C. (from methanol).

EXAMPLE 2

Preparation of 2,4-diamino-5-(4-isopropenyl-3,5-dimethoxybenzyl)-pyrimidine

A solution of 5.0 mg. of 4-[(4-acetylamino-2-amino-5-pyrimidyl)-methyl]-2,6-dimethoxy-α,α-dimethylbenzyl alcohol was warmed under reflux for 1 hour in 1 ml. of concentrated hydrochloric acid. After cooling, the mixture was adjusted to pH 10 with concentrated aqueous ammonia and extracted three times with 2 ml. of ethyl acetate each time. The extract was dried and evaporated. The residue yielded, after recrystallization from methanol, 3.2 mg. of 2,4-diamino-5-(4-isopropenyl-3,5-dimethoxybenzyl)-pyrimidine, having a melting point of 228°–229° C.

EXAMPLE 3

Preparation of 2,4-diamino-5-(4-isopropenyl-3,5-dimethoxybenzyl)-pyrimidine

A suspension of 280.7 mg. of guanidine carbonate, 162 mg. of sodium methylate and 273 mg. of 4-isopropenyl-3,5-dimethoxy-α-(methoxymethylene)-dihydrocinnamic acid nitrile was heated to reflux for 18 hours while stirring. The solvent was then removed under reduced pressure. The residue was stirred with 20 ml. of water for 30 minutes and the solid crude product was removed by filtration under suction. After recrystallization from methanol, there were obtained 180 mg. (60%) of 2,4-diamino-5-(4-isopropenyl-3,5-dimethoxybenzyl)-pyrimidine, having a melting point of 228°–229° C.

The starting material was prepared as follows:

10 Ml. of methanol and 10 ml. of 2-N hydrochloric acid were added to a solution of 22.4 g. of 4-(2-hydroxy-2-propyl)-3,5-dimethoxybenzaldehyde in 150 ml. of benzene. The mixture was heated to reflux for 2 hours while gassing with nitrogen, brought to dryness under reduced pressure and the residue was recrystallized from n-heptane. There were obtained 15 g. of 4-isopropenyl-3,5-dimethoxybenzaldehyde having a melting point of 97°–98° C.

A solution of 1 g. of 4-isopropenyl-3,5-dimethoxybenzaldehyde, 0.375 g. of β-methoxy-propionitrile and 0.1 g. of sodium methylate in 5 ml. of methanol was heated under reflux for 24 hours. The solvent was removed, the residue was dissolved in 10 ml. of benzene and 5 ml. of water and the benzene phase was separated, repeatedly washed with water, dried and concentrated. There was obtained 0.92 g. of 4-isopropenyl-3,5-dimethoxy-α-(methoxymethylene)-dihydrocinnamic acid nitrile which melted at about 40° C. after purification by chromatography on silica gel with ether.

EXAMPLE 4

Preparation of 2,4-diamino-5-(4-isopropenyl-3,5-dimethoxybenzyl)-pyrimidine 2.85 G. of guanidine carbonate and 3.5 g. of 4-isopropenyl-3,5-dimethoxy-α-(anilinomethylene)-dihydrocinnamic acid nitrile were added to a solution of 0.73 g. of metallic sodium in 25 ml. of ethanol and the suspension was heated to reflux for 18 hours while stirring. The solvent was removed under reduced pressure, the residue was stirred with 50 ml. of water and removed by filtration under suction. After recrystallization from methanol, there were obtained 2.9 g. (83%) of 2,4-diamino-5-(4-isopropenyl-3,5-dimethoxybenzyl)-pyrimidine, having a melting point of 228°–229° C.

The starting material was prepared as follows:

0.54 G. of sodium methylate was added to a solution, warmed to 60° C., of 10.3 g. of 4-isopropenyl-3,5-dimethoxy-benzaldehyde and 7.7 g. of β-morpholino-propionitrile in 8 ml. of anhydrous dimethylsulfoxide. While the temperature rose to 70° C., the mixture was stirred for an additional 15 minutes, cooled to 15° C., diluted with 10 ml. of isopropanol and treated dropwise, while cooling with ice-water, with a total of 40 ml. of water. The resulting suspension was stirred at 0°–5° C. for 2 hours and filtered. The residue was washed with a cold mixture of isopropanol and water (1:4, v/v). After drying, there were obtained 13.3 g. of 4-isopropenyl-3,5-dimethoxy-α-(morpholinomethylene)-dihydrocinnamic acid nitrile, having a melting point of 124°–125° C. (from methanol).

A suspension of 2.4 g. of aniline, 2.2 ml. of concentrated hydrochloric acid and 8.5 g. of 4-isopropenyl-3,5-dimethoxy-α-(morpholinomethylene)-dihydrocinnamic acid nitrile in 30 ml. of isopropanol was heated to reflux while stirring for 1 hour. After cooling, the crystalline 4-isopropenyl-3,5-dimethoxy-α-(anilinomethylene)-dihydrocinnamic acid nitrile, melting point 188°–191° C. (from methanol), was removed by filtration under suction and dried (yield 83%).

EXAMPLE 5

Preparation of 2,4-diamino-5-(4-isopropenyl-3,5-dimethoxybenzyl)-pyrimidine

A suspension of 164 mg. of 4-isopropenyl-3,5-dimethoxy-α-(morpholinomethylene)-dihydrocinnamic acid nitrile and 0.17 g. of guanidine carbonate in 0.25 ml. of dimethylsulfoxide was warmed to 160° C. while stirring for 3 hours. After cooling, the mixture was treated with 1.5 ml. of ice-water and stirred for 1 hour. The solid crude product was filtered off under suction, washed with a small amount of water and acetone and then dried. After recrystallization from methanol, there was obtained pure 2,4-diamino-5-(4-isopropenyl-3,5-dimethoxybenzyl)-pyrimidine, having a melting point of 228°–229° C.

EXAMPLE 6

Preparation of 2,4-diamino-5-(3,5-diethoxy-4-isopropenylbenzyl)-pyrimidine 5.5 G. of 3,5-diethoxy-4-isopropenyl-α-(anilinomethylene)-dihydrocinnamic acid nitrile and 8.1 g. of guanidine carbonate were added to a sodium ethylate solution freshly prepared from 1 g. of sodium and 50 ml. of ethanol. The mixture was heated under reflux for 60 hours, the solvent was removed, the residue was suspended in ice-water, filtered under suction and the crystalline crude product was recrystallized from ethyl acetate/petroleum ether. There was obtained 4.5 g. of 2,4-diamino-5-(3,5-diethoxy-4-isopropenylbenzyl)-pyrimidine, having a melting point of 197°–198° C.

The starting material was prepared as follows:

A solution of 24 g. of ethyl 2,6-diethoxy-4-formylbenzoate in 100 ml. of ethanol, 13.2 g. of ethyl orthoformate and 1 ml. of concentrated hydrochloric acid was heated under reflux for 2 hours and subsequently concentrated under reduced pressure. The oily residue, dissolved in 500 ml. of ether, was added dropwise to a Grignard solution prepared from 6.5 g. of magnesium, 42.6 g. of methyl iodide and 240 ml. of ether. The mixture was heated under reflux for 3 hours, cooled to room temperature and treated with 30 ml. of water and with 30 ml. of 3-N sodium hydroxide. The ethereal phase was separated, washed with 30 ml. of 3-N sodium hydroxide and the aqueous phases were exhaustively extracted with ether. The combined organic phases were concentrated to 150 ml., treated with 60 ml. of 1-N hydrochloric acid and shaken at room temperature for 15 minutes. Working-up of the ethereal phase yielded 21 g. of 3,5-diethoxy-4-isopropenylbenzaldehyde, having a melting point of 60° C.

A solution of 11 g. of 3,5-diethoxy-4-isopropenylbenzaldehyde and 7 g. of β-morpholino-propionitrile in 100 ml. of dimethylformamide was warmed to 60° C. After the addition of 1.1 g. of sodium methylate, the mixture was stirred for 30 minutes, the solvent was distilled, the residue was removed by filtration under suction and washed twice with 100 ml. of ether each time. There were obtained 12.5 g. of 3,5-diethoxy-4-isopropenyl-α-(morpholinomethylene)-dihydrocinnamic acid nitrile, having a melting point of 75°–80° C. (from ethyl acetate/petroleum ether).

A solution of 12 g. of 3,5-diethoxy-4-isopropenyl-α-(morpholinomethylene)dihydrocinnamic acid nitrile in 20 ml. of isopropanol was added to an ice-cold mixture of 3.6 ml. of aniline and 2.25 ml. of acetic acid. The mixture was warmed to 80° C. for 90 minutes, treated with 40 ml. of water, cooled to 10° C. and filtered under suction. After washing with water and ether, the crystalline residue yielded 9.5 g. of 3,5-diethoxy-4-isopropenyl-α-(anilinomethylene)-dihydrocinnamic acid nitrile, having a melting point of 176°–178° C.

EXAMPLE 7

Preparation of 2,4-diamino-5-(3-ethoxy-4-isopropenyl-5-methoxybenzyl)-pyrimidine A mixture of 9.4 g. of 2,4-diamino-5-(3-hydroxy-4-isopropenyl-5-methoxybenzyl)-pyrimidine, 65.6 ml. of 1-N sodium hydroxide, 130 ml. of 50% aqueous ethanol and 11.12 g. of diethyl sulfate was stirred at room temperature for 2 hours. The ethanol was then evaporated, the residue was diluted with 50 ml. of water, made alkaline with concentrated ammonia and the crude product was removed by filtration under suction. After recrystallization from methanol, there were obtained 5.5 g. of 2,4-diamino-5-(3-ethoxy-4-isopropenyl-5-methoxybenzyl)-pyrimidine, having a melting point of 197°–199° C.

The starting material was prepared as follows:

A solution of 16.1 ml. of ethylmercaptan in 130 ml. of dimethylformamide was added dropwise while stirring and gassing with nitrogen to a suspension of 10.4 g. of sodium hydride (50%) in 130 ml. of dimethylformamide. After the evolution of gas had ceased, the mixture was stirred at room temperature for an additional 15 minutes and treated with a solution 13 g. of 2,4-diamino-5-(4-isopropenyl-3,5-dimethoxybenzyl)-pyrimidine in 260 ml. of dimethylformamide. The mixture was stirred at 120° C. for 6 hours. The solvent was removed under a high vacuum. The solid residue was dissolved in water, filtered and the filtrate was adjusted to pH 4 with 1-N hydrochloric acid. The acid solution was then adjusted to pH 8 with ammonia and the solid crude product was isolated in a yield of 98%. Recrystallization from methanol yielded pure 2,4-diamino-5-(3-hydroxy-4-isopropenyl-5-methoxybenzyl)-pyrimidine, having a melting point of 218°–219° C.

EXAMPLE 8

Preparation of 2,4-diamino-5-{3,5-dimethoxy-4-[3-(2-pentenyl)]-benzyl}-pyrimidine A suspension of 4 g. of 4-[(2,4-diamino-5-pyrimidyl)-methyl]-2,6-dimethoxy-α,α-diethylbenzyl alcohol in 72 ml. of ethanol and 7.2 ml. of concentrated hydrochloric acid was heated to reflux for 3 hours while stirring and subsequently evaporated to dryness under reduced pressure. The residue was suspended in 100 ml. of water. The suspension was made alkaline (pH about 10) with aqueous ammonia and stirred for a further 2 hours. The crystalline product was again stirred with 50 ml. of water, filtered under suction and recrystallized from ethanol. There were obtained 3.1 g. (78%) of 2,4-diamino-5-{3,5-dimethoxy-4-[3-(2-pentenyl)]-benzyl}-pyrimidine, having a melting point of 197°–199° C.

EXAMPLE 9

Preparation of 2,4-diamino-5-(3,5-diethoxy-4-isopropenylbenzyl)-pyrimidine

A solution of 2 g. of 4-[(2,4-diamino-5-pyrimidyl)-methyl]-2,6-diethoxy-α,α-dimethylbenzyl alcohol in 40 ml. of methanol and 4 ml. of concentrated hydrochloric acid was heated under reflux for 2 hours. The solvent was distilled. The residue was suspended in water and the suspension, after the addition of 25% ammonia solution up to a pH of about 10, was stirred for about 1 hour. The crystalline residue was removed by filtration under suction, washed neutral with water and dried. After recrystallization from ethyl acetate, there were obtained 1.9 g. of colorless 2,4-diamino-5-(3,5-diethoxy-4-isopropenylbenzyl)-pyrimidine having a melting point of 196°–198° C.

EXAMPLE 10

Preparation of 2,4-diamino-5-(4-isopropenyl-3,5-dimethoxybenzyl)-pyrimidine hydrochloride 3.3 Ml. of 1-N hydrochloric acid were added to a solution of 0.9 g. of 2,4-diamino-5-(4-isopropenyl-3,5-dimethoxybenzyl)-pyrimidine in 100 ml. of methanol. The solution was concentrated to 25 ml. and, after cooling, the crystals were removed by filtration under suction and dried. The resulting 2,4-diamino-5-(4-isopropenyl-3,5-dimethoxybenzyl)-pyrimidine hydrochloride melts at above 300° C.

EXAMPLE 11

Preparation of 2,4-diamino-5-(4-isopropenyl-3,5-dimethoxybenzyl)-pyrimidine lactate 4.5 G. of 2,4-diamino-5-(4-isopropenyl-3,5-dimethoxybenzyl)-pyrimidine and 1.9 g. of 72.5% lactic acid were dissolved in 250 ml. of water. The solution was filtered, concentrated to half volume, cooled and the crystalline 2,4-diamino-5-(4-isopropenyl-3,5-dimethoxybenzyl)-pyrimidine lactate, melting point 287°–290° C. (decomposition), was removed by filtration under suction.

EXAMPLE 12

Preparation of 2,4-diamino-5-(3,5-dimethoxy-4-isopropenylbenzyl)-pyrimidine

About 2 ml. of solvent were distilled under reduced pressure from a mixture of 0.8 g. of α-(aminomethylene)-3,5-dimethoxy-4-isopropenylhydrocinnamic acid nitrile, 0.56 g. of guanidine carbonate, 170 g. of potassium hydroxide, 1.5 ml. of water and 10 ml. of isoamyl alcohol. The mixture remaining was stirred under reflux at 135° C. for 24 hours. After evaporation to dryness, the residue was stirred with ether and then with water. The product was filtered under suction and recrystallized from methanol. There was obtained 0.11 g. of 2,4-diamino-5-(3,5-dimethoxy-4-isopropenylbenzyl)-pyrimidine, having a melting point of 226°–229° C.

The starting material was prepared as follows:

A mixture of 10.3 g. of 3,5-dimethoxy-4-isopropenylbenzaldehyde, 6.7 g. of malonic acid dinitrile and 2 drops of piperidine was heated to 120° C. for 90 minutes while gassing with nitrogen and stirring, cooled and recrystallized from methanol. There was obtained in 80% yield α-cyano-3,5-dimethoxy-4-isopropenylcinnamic acid nitrile, having a melting point of 129°–131° C.

200 Mg. of sodium borohydride were added portionwise at room temperature while stirring to a suspension of 2.5 g. of α-cyano-3,5-dimethoxy-4-isopropenylcinnamic acid nitrile in 75 ml. of ethanol and 2 drops of 1-N sodium hydroxide. After stirring for 4 hours, the solution was evaporated. The residue was suspended in water and the suspension was extracted with ether. The ether extract was dried and evaporated to dryness. Column chromatography of the crude product (2.6 g.) on silica gel with benzene/methanol (9:1, v/v) yielded α-(aminomethylene)-3,5-dimethoxy-4-isopropenylhydrocinnamic acid nitrile, having a melting point of 122°–125° C. (from ether).

EXAMPLE 13

Preparation of 2,4-diamino-5-(3,5-dimethoxy-4-isopropenylbenzyl)-pyrimidine

A mixture of 167.7 mg. of 2,6-diamino-4-chloro-5-(3,5-dimethoxy-4-isopropenylbenzyl)-pyrimidine, 1.6 ml. of glacial acetic acid, 10 mg. of mercury (II) chloride, 0.2 ml. of water and 150 mg. of zinc powder was boiled under reflux overnight while stirring. The solution was filtered while hot, unreacted zinc was washed out with 0.5 ml. of glacial acetic acid. The filtrate was diluted with 2 ml. of water, made alkaline with concentrated ammonia solution while cooling and extracted three times with 5 ml. of ethyl acetate each time. The extract was dried and concentrated and the residue was recrystallized from methanol. There were obtained 148 mg. (73%) of 2,4-diamino-5-(3,5-dimethoxy-4-isopropenylbenzyl)-pyrimidine, having a melting point of 226°–229° C.

The starting material was prepared as follows:

A mixture of 10.3 g. of 3,5-dimethoxy-4-isopropenylbenzaldehyde, 6.7 g. of ethyl cyanoacetate and 2 drops of piperidine was heated to 120° C. for 90 minutes in an open flask while stirring, cooled and recrystallized from n-heptane. There were obtained 12.8 g. (85%) of ethyl α-cyano-3,5-dimethoxy-4-isopropenylcinnamate, having a melting point of 100°–102° C.

0.14 G. of sodium borohydride was added while stirring to a suspension of 4.3 g. of ethyl α-cyano-3,5-dimethoxy-4-isopropenylcinnamate in 80 ml. of ethanol and 2 drops of 1-N sodium hydroxide, a solution resulting. After 30 minutes, the ethanol was removed under a water-jet vacuum at 40° C., the residue was taken up in ether, the solution was washed with water and filtered through silica gel. There were obtained 3.4 g. (79.1%) of ethyl α-cyano-3,5-dimethoxy-4-isopropenylhydrocinnamate, having a melting point of 55° C. 2.3 G. of guanidine hydrochloride were added to a solution of 0.55 g. of sodium in 40 ml. of absolute ethanol. After 30 minutes, the suspension was filtered and 3.5 g. of ethyl α-cyano-3,5-dimethoxy-4-isopropenylcinnamate were added to the filtrate. The mixture was boiled under reflux for 18 hours and evaporated to dryness. The residue was triturated several times with ether and then with water and filtered under suction. There were obtained 1.6 g. (44%) of 2,6-diamino-5-(3,5-dimethoxy-4-isopropenylbenzyl)-4-pyrimidinol, having a melting point of 256°–258° C.

0.65 G. of dimethylaniline was added dropwise while stirring to a suspension of 0.8 g. of 2,6-diamino-5-(3,5-dimethoxy-4-isopropenylbenzyl)-4-pyrimidinol in 6.5 g. of phosphorus oxychloride. The mixture was boiled for 4 hours while stirring and then about half of the phosphorus oxychloride was distilled under reduced pressure. About 10 g. of ice were added to the residue. The suspension was left to stand at room temperature for 2 days, adjusted to pH 10 with concentrated ammonia solution and the precipitate was filtered under suction 2 hours later. The precipitate was freed from dimethylaniline by steam distillation. After cooling the aqueous suspension, the resulting crude 2,6-diamino-4-chloro-5-(3,5-dimethoxy-4-isopropenylbenzyl)-pyrimidine was chromatographed on silica gel with benzene/methanol (9:1, v/v) and, after evaporation of the solvents, recrystallized from methanol. Yield: 0.27 g. (32%); melting point 199°–200° C.

The following Examples illustrate pharmaceutical preparations provided by the present invention:

Example A

| Tablets, each containing the following ingredients: | |
| --- | --- |
| 2,4-Diamino-5-(3,5-dimethoxy-4-isopropenyl-benzyl)-pyrimidine | 80.00 mg. |
| Pregelatinized starch | 12.50 mg. |
| Sodium carboxymethyl starch | 12.50 mg. |
| Lactose (powdered) | 131.25 mg. |
| Maize starch | 12.50 mg. |
| Magnesium stearate | 1.25 mg. |
| | 250.00 mg. | were produced by moist granulating a mixture of the aforementioned ingredients with the addition of water, drying the resulting granulate and pressing the dried granulate into tablets.

Example B

| An injection solution contains per ml: | |
| --- | --- |
| 2,4-Diamino-5-(3,5-dimethoxy-4-isopropenyl-benzyl)-pyrimidine | 20.0 mg. |
| Glycofurol | 0.3 ml. |
| Lactic acid ad pH 4.0 | q.s. |
| Water | ad 1.0 mg. |

The solution was sterilized at 120° C. for 20 minutes.

We claim:

1. A compound of the formula

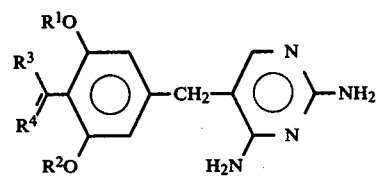

I wherein $R^1$ and $R^2$, independently, are $C_{1-6}$-alkyl, $R^3$ is $C_{1-3}$-alkyl and $R^4$ is methylene or $C_{2-4}$-alkylidene, or a physiologically acceptable acid addition salt thereof.

2. A compound in accordance with claim 1, wherein $R^1$ and $R^2$, independently, are $C_{1-3}$-alkyl.

3. A compound in accordance with claim 1, wherein each of $R^1$ and $R^2$ is methyl.

4. A compound in accordance with claim 1, wherein each of $R^1$ and $R^2$ is ethyl.

5. A compound in accordance with any one of claims 1, 2, 3 or 4, inclusive, wherein $R^3$ is methyl.

6. A compound in accordance with any one of claims 1, 2, 3 or 4, inclusive, wherein $R^3$ is ethyl.

7. A compound in accordance with any one of claims 1, 2, 3 or 4, inclusive, wherein $R^3$ is propyl or isopropyl.

8. A compound in accordance with any one of claims 1, 2, 3 or 4, inclusive, wherein $R^4$ is methylene.

9. A compound in accordance with any one of claims 1, 2, 3 or 4, inclusive, wherein $R^4$ is ethylidene.

10. A compound in accordance with claim 1, 2,4-diamino-5-(4-isopropenyl-3,5-dimethoxybenzyl)-pyrimidine.

11. A compound in accordance with claim 1, 2,4-diamino-5-(3,5-diethoxy-4-isopropenylbenzyl)-pyrimidine.

12. A compound in accordance with claim 1, 2,4-diamino-5-(3-ethoxy-4-isopropenyl-5-methoxybenzyl)-pyrimidine.

13. A compound in accordance with claim 1, 2,4-diamino-5-{3,5-dimethoxy-4-[3-(2-pentenyl)]benzyl}-pyrimidine.

14. An antibacterial pharmaceutical composition comprising a compound of the formula

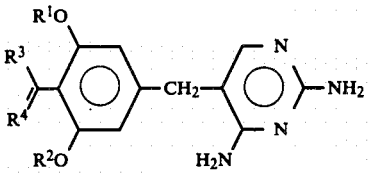

wherein $R^1$ and $R^2$, independently, are $C_{1-6}$-alkyl, $R^3$ is $C_{1-3}$-alkyl and $R^4$ is methylene or $C_{2-4}$-alkylidene, or a pharmaceutically acceptable acid addition salt thereof, an antibacterially active sulfonamide and a compatible pharmaceutical carrier material, said compound of formula I being present in an amount sufficient to potentiate the antibacterial activity of the sulfonamide.

15. An antibacterial pharmaceutical composition in accordance with claim 14 comprising a compound of the formula

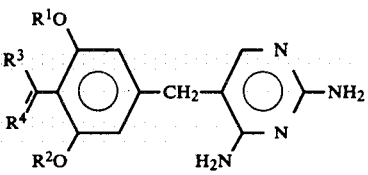

wherein $R^1$ and $R^2$, independently, are $C_{1-6}$-alkyl, $R^3$ is $C_{1-3}$-alkyl and $R^4$ is methylene or $C_{2-4}$-alkylidene, or a pharmaceutically acceptable acid addition salt thereof, an antibacterially active sulfonamide and a compatible pharmaceutical carrier material, the ratio of said compound of formula (I) to said antibacterially active sulfonamide in the composition being from 1:40 to 10:1.

16. An antibacterial pharmaceutical composition in accordance with claim 15 wherein the ratio of said compound of formula (I) to said antibacterially active sulfonamide is from 1:5 to 5:1.

* * * * *